(12) United States Patent
Lin et al.

(10) Patent No.: US 9,907,773 B2
(45) Date of Patent: Mar. 6, 2018

(54) USE OF NOVEL MONOSACCHARIDE-LIKE GLYCYLATED SUGAR ALCOHOL COMPOSITIONS FOR DESIGNING AND DEVELOPING ANTI-DIABETIC DRUGS

(71) Applicants: Shi-Lung Lin, Arcadia, CA (US); Samantha Chang-Lin, Arcadia, CA (US); Yi-Wen Lin, Santa Fe Spring, CA (US); Donald Chang, Cerritos, CA (US)

(72) Inventors: Shi-Lung Lin, Arcadia, CA (US); Samantha Chang-Lin, Arcadia, CA (US); Yi-Wen Lin, Santa Fe Spring, CA (US); Donald Chang, Cerritos, CA (US)

(*) Notice: Subject to any disclaimer, the term of this patent is extended or adjusted under 35 U.S.C. 154(b) by 43 days.

(21) Appl. No.: 15/074,321

(22) Filed: Mar. 18, 2016

(65) Prior Publication Data

US 2016/0220525 A1 Aug. 4, 2016

Related U.S. Application Data

(60) Division of application No. 14/585,978, filed on Dec. 30, 2014, which is a continuation-in-part of application No. 14/457,829, filed on Aug. 12, 2014.

(60) Provisional application No. 61/931,650, filed on Jan. 26, 2014, provisional application No. 62/050,107, filed on Sep. 13, 2014, provisional application No. 62/054,981, filed on Sep. 25, 2014.

(51) Int. Cl.
| | |
|---|---|
| *A61K 31/221* | (2006.01) |
| *A61K 9/08* | (2006.01) |
| *A61K 31/7024* | (2006.01) |
| *A61K 9/00* | (2006.01) |
| *A61K 31/7012* | (2006.01) |
| *C12N 15/11* | (2006.01) |
| *C12N 15/113* | (2010.01) |

(52) U.S. Cl.
CPC .......... *A61K 31/221* (2013.01); *A61K 9/0053* (2013.01); *A61K 9/08* (2013.01); *A61K 31/7012* (2013.01); *A61K 31/7024* (2013.01); *C12N 15/111* (2013.01); *C12N 15/113* (2013.01); *C12N 2310/141* (2013.01); *C12N 2320/32* (2013.01); *C12N 2330/50* (2013.01); *C12N 2330/51* (2013.01)

(58) Field of Classification Search
None
See application file for complete search history.

(56) References Cited

U.S. PATENT DOCUMENTS

| 5,618,933 A | 4/1997 | Dordick et al. |
| 6,251,599 B1 | 6/2001 | Chen et al. |
| 2014/0350085 A1 | 11/2014 | Lin et al. |

FOREIGN PATENT DOCUMENTS

| EP | 0 535 534 A1 | 4/1993 |
| WO | WO 2002/032398 A2 | 4/2002 |
| WO | WO 2007/133616 A2 | 11/2007 |
| WO | WO 2009/029046 A1 | 3/2009 |
| WO | WO 2011/143237 A1 | 11/2011 |
| WO | WO 2015/099839 | * 8/2014 |

OTHER PUBLICATIONS

Arsequell, G., et al, "9-Fluorenylmethoxycarbonyl (Fmoc)-Glycine Coupling of Saccharide•-Glycosylamines for Fractionation of Oligosaccharides and the Formation of Neoglycoconjugates," Analytical Biochemistry, Jan. 1, 1994, vol. 216, No. 1, pp. 165-170.
Banerjee et al., "Drug delivery system: targeting of pentamidines to specific sites using sugar grafted liposomes", Journal of Antimicrobial Chemotherapy 38, pp. 145-150, (1996).
Bhatia et al., Abstract of "Biocatalytic route to sugar-PEG-based polymers for drug delivery applications", Biomacromolecules 12, pp. 1-18, 2011.
Blanchfield et al., "Lipid, Sugar and Liposaccharide Based Delivery Systems 2", Current Medicinal Chemistry 11, pp. 2375-2382, 2004.
Chen et al., "Recent Patents on MicroRNA-Induced Pluripotent Stem Cell Generation", Recent Patents on Regenerative Medicine 3, pp. 5-16, (2013).
Chrzaszczewska, A. et al, "The diacylglycerophosphoric acids. III. Glycine esters," Acta Chim., 1962, vol. 8, pp. 29-35.
Cūna et al., Abstract of "Development of phosphorylated glucomannan-coated chitosan nanoparticles as nanocarriers for protein delivery", J Nanotechnol 6, 2006.
Davis et al., "Drug delivery systems based on sugar-macromolecule conjugates" Current Opinion in Drug Discovery & Development 5(2), pp. 279-288, 2002.
Davis et al., "Evidence of RNAi in humans from systemically administered siRNA via targeted nanoparticles", Nature 464, pp. 1067-1070, 2010.
Ellis et al., "Boronate-Mediated Biologic Delivery", Journal of the American Chemical Society 134, pp. 3631-3634, (2012).
Gannon, M.C. et al., "The metabolic response to ingested glycine," Am. J. Clin. Nutr., Jan. 1, 2002, vol. 76, pp. 1302-1307.
Gao et al., Abstract of "Aminated Linear and Star-Shape Poly(glycerol methacrylate)s: Synthesis and Self-Assembling Properties", Biomacromolecules. 11, pp. 889-895, 2010.
Gao et al., Abstract of "Amino poly(glycerol methacrylate)s for oligonucleic acid delivery with enhanced transfection efficiency and low cytotoxicity", Soft Matter 7, 2011.

(Continued)

*Primary Examiner* — James D Schultz
(74) *Attorney, Agent, or Firm* — Birch, Stewart, Kolasch & Birch, LLP (57) ABSTRACT

This invention is related to a novel sugar-like chemical composition and its use for diabetes therapy. Particularly, the present invention teaches the use of monosaccharide-like glycylated sugar alcohol compounds to block or reduce sugar absorption in diabetes patients, so as to prevent the risk of hyperglycemia symptoms. Glycylation of sugar alcohols is a totally novel reaction that has never been reported before. Therefore, the novelty of the present invention is that for the first time glycylated sugar alcohols not only was found but also was found to be useful for treating Diabetes mellitus. In addition, the present invention teaches a method for producing these glycylated sugar alcohols. In sum, the present invention includes not only a kind of novel sugar-like chemical compositions and its use for treating diabetes but also a state-of-the-art protocol and methodology for producing such a novel composition via glycylation of sugars and sugar alcohols.

15 Claims, 6 Drawing Sheets

(56) References Cited

OTHER PUBLICATIONS

Graf et al., Abstract of "Microemulsions containing lecithin and sugar-based surfactants: nanoparticle templates for delivery of proteins and peptides", Int J Pharm. 350, 2008.

Immordino et al., "Stealth liposomes: review of the basic science, rationale, and clinical applications, existing and potential", Int J Nanomedicine1, pp. 297-315, 2006.

International Search Report and Written Opinion of the International Searching Authority, (Forms PCT/ISA/220, PCT/ISA/210 and PCT/ISA/237), dated Nov. 17, 2014, for International Application No. PCT/US2014/050114.

International Search Report for Appl. No. PCT/US2014/072693 dated Apr. 20, 2015.

Kinomura, K. et al., "Synthesis of Methyl-2,3-Di-O-Glycly-•-D-Glucopyranoside and 4,6-Di-O-Glycly-2,3-Di-O-Methyl-•-D-Glucopyranoside, and removal of aminoacyl groups from sugar moieties," J. Carbohydrate Chemistry, Jan. 1, 1984, vol. 3, No. 2, pp. 229-241.

Lin et al., "Loss of mir-146a function in hormone-refractory prostate cancer", RNA 14, No. 3, pp. 417-424, 2008.

Lin et al., "MicroRNA miR-302 Inhibits the Tumorigenecity of Human Pluripotent Stem Cells by Coordinate Suppression of the CDK2 and CDK4/6 Cell Cycle Pathways", Cancer Res, vol. 70, No. 22, Nov. 15, 2010 (published online Nov. 9, 2010), pp. 9473-9482.

Lin et al., "Mir-302 reprograms human skin cancer cells into a pluripotent ES-cell-like state", RNA 2008, vol. 14, No. 10, Aug. 28, 2008, pp. 2115-2124.

Lin et al., "Regulation of somatic cell reprogramming through inducible mir-302 expression", Nucleic Acids Research, vol. 39, No. 3, 2011, (published online Sep. 24, 2010), pp. 1054-1065.

Morris et al., "Polysaccharide drug delivery systems based on pectin and chitosan", Biotechnology and Genetic Engineering Reviews 27, 257-284 (2010).

Pereira et al., "Glycerol monooleate/solvents systems for progesterone transdermal delivery: in vitro permeation and microscopic studies", Brazilian Journal of Pharmaceutical Sciences 38, pp. 55-62.

Weizmann, M. et al, "Attempts to prepare esters of glycerol and amino acids, as the mixed esters of amino acids and fatty acids. 1st part," Bulletin de la Societe Chimique de France, Societe Francaise de Chimie, Jan. 1, 1932, vol. 51, No. 4, pp. 59-73.

Written Opinion of the International Searching Authority for Appl. No. PCT/US2014/072693 dated Apr. 20, 2015.

Zhen et al., Abstract of "Glycerol monooleate-based nanocarriers for siRNA delivery in vitro", Mol. Pharm., pp. 2450-2457, 2012.

* cited by examiner

FIG. 1

FIG. 2A glycerol (glycerin)    glycine

+

*Glycylation of Sugar Alcohols (i.e. glycerol)*

1-monoglycylglycerin (1-MGG)

or

3-monoglycylglycerin (3-MGG)

or

2-monoglycylglycerol (2-MGG)

USE OF NOVEL MONOSACCHARIDE-LIKE GLYCYLATED SUGAR ALCOHOL COMPOSITIONS FOR DESIGNING AND DEVELOPING ANTI-DIABETIC DRUGS

PRIORITY

The present application is a Divisional of U.S. patent application Ser. No. 14/585,978 filed on Dec. 30, 2014, entitled "The Use of Novel Monosaccharide-like Glycylated Sugar Alcohol Compositions for Designing and Developing Anti-Diabetic Drugs," which is a continuation-in-part (CIP) application of U.S. patent application Ser. No. 14/457,829 filed on Aug. 12, 2014, entitled "Novel Sugar Alcohol-Based Compositions for Delivering Nucleic Acid-Based Drugs In Vivo and In Vitro". U.S. patent application Ser. No. 14/585,978 claims priority to U.S. Provisional Application Ser. No. 61/931,650 filed on Jan. 26, 2014, entitled "Composition and Formulation of Sugar Alcohol-Based Complexes for Delivering Nucleic Acid-Based Drugs In Vitro and In Vivo"; U.S. Provisional Application Ser. No. 62/050,107 filed on Sep. 13, 2014, entitled "Novel Monosaccharide-like Glycylated Sugar Alcohol Compositions useful for Diabetes Therapy"; and U.S. Provisional Application Ser. No. 62/054,981 filed on Sep. 25, 2014, entitled "Novel Monosaccharide-like Glycylated Sugar Alcohol Compositions useful for Diabetes Therapy", which are hereby all incorporated by reference as if fully set forth herein.

FIELD OF INVENTION

This invention generally relates to a novel sugar-like chemical composition and its use for diabetes therapy. Particularly, the present invention teaches the use of monosaccharide-like modified sugar alcohol compositions to replace sugars for absorption in patients, so as to treat diabetes mellitus. In order to mimic monosaccharides, these novel sugar alcohol compositions are modified by a reaction called glycylation and turned into glycylated sugar alcohols. As a result, the novelty of the present invention is to use these glycylated sugar alcohols for reducing the sugar uptake in human intestines, subsequently preventing the hyperglycemia symptoms of diabetes patients after meals. In addition, the present invention teaches for the first time that chemical compounds like sugar alcohols and sugars can be modified by glycylation to reduce their pathological effects in diabetes. Therefore, the present invention includes not only a kind of novel sugar-like chemical compositions and its use for treating diabetes but also a state-of-the-art protocol and methodology for producing such a novel composition via glycylation.

BACKGROUND

Diabetes mellitus (DM), also known as diabetes, is a group of metabolic diseases that cause long-lasting hyperglycemia symptoms in humans as well as some other mammals, such as mice. These hyperglycemia symptoms include high blood sugar levels (i.e. >140 mg/dL), frequent urination, increased thirst and hunger, and more severely diabetic ketoacidosis and hyperosmolar coma. Long-term hyperglycemia often leads to heart diseases, stroke, kidney failure, ulcers in extremities, eye damages and obesity. There are two types of diabetes: type-I DM results from lack of sufficient insulin production in pancreas (or called insulin-dependent DM; IDDM), and type-II DM results from body's failure to respond to insulin (or called insulin resistance; non-insulin-dependent DM; NIDDM). For treatment, type-I DM must be managed with insulin injections while type-II DM may or may not be treated with insulin, depending on the pathological causes of insulin resistance.

Current medications for type-II DM can be categorized into five groups: first, drugs increase insulin production in pancreas, such as Sulfonylureas, Meglitinides and Stitagliptin; second, drugs decrease sugar production in liver, such as Metformin; third, drugs increase sugar excretion via urine, such as Canagliflozin; forth, drugs reduce insulin resistance in fat tissues and muscles, such as Thiazolidinediones; and last, drugs delay and/or reduce sugar absorption in intestines, such as alpha-glucosidase inhibitors. However, due to the kinetic properties of these drugs directed against certain natural metabolic pathways of the body, they often present various degrees of side effects, including hypoglycemia (Sulfonylureas, Meglitinides, Stitagliptin and alpha-glucosidase inhibitors), kidney failure (Metformin and Canagliflozin), heart failure (Metformin and Thiazolidinediones), gastrointestinal problems (Metformin and alpha-glucosidase inhibitors), edema and anemia (Thiazolidinediones). In some worst cases, death has been reported.

To prevent the lethal problems of kidney and heart failure, the best way of treating type-II diabetes is to delay and reduce sugar absorption in intestines; yet, without losing the supply of energy. The current anti-diabetic drugs of this kind such as alpha-glucosidase inhibitors function through inhibition of intestinal enzymes that convert carbohydrates into monosaccharides and hence can block sugar uptake in intestines. Nevertheless, the undigested carbohydrates may then interact with colon bacteria to cause gastrointestinal problems, such as flatulence and diarrhea. From the beneficial view, this side effect may help to reduce obesity; yet, the drawback is that blocking sugar uptake also means loss of energy supply to the body. As a result, overdose of alpha-glucosidase inhibitors can lead to acute hypoglycemia in diabetes patients.

Recently, it is further noted that the use of sugars and sugar substitutes such as artificial sweeteners may worsen the sugar intolerance conditions of Diabetes mellitus in patients (Suez et al., (2014) Nature in press, doi:10.1038/nature13793).

In sum, there is currently no safe drug agent or sugar substitute that can treat type-II DM while still maintaining the supply of normal body energy. Therefore, it is highly desirable to have a novel anti-diabetic composition that is able not only to reduce sugar absorption in intestines but also to provide an alternative energy source to the body.

SUMMARY OF THE INVENTION

Stem cells are treasure boxes containing various effective ingredients useful for designing and developing cosmedical, pharmaceutical and therapeutic drugs and/or applications, including, but not limited by, inducing and enhancing body cell/tissue/organ regeneration, repairing/healing damaged tissues and organs, rejuvenating aged cells/tissues/organs, treating degenerative diseases (i.e. cancers, diabetes, osteoporosis, Parkinson's and Alzheimer's diseases . . . etc), and preventing tumor/cancer formation, progression and/or metastasis. In view of these potentials, the inventors had developed a novel technology to generate microRNA-induced pluripotent stem cells (iPSCs) in early 2008 (Lin et al., 2008, 2010 and 2011) and then successfully used these iPSCs as a tool for screening, identifying, isolating, and producing potential drug ingredients for clinical testing and use (Chen and Lin, (2013) *Recent Patents on Regenerative Medicine* 3, 5-16).

Sugar alcohols are a generic kind of polyol alcohols derived from sugars and also frequently called polyhydric alcohol, polyalcohol, or glycitol; sugar alcohols have been found to be abundantly glycylated in early stage iPSCs as well. As defined in polymer chemistry, polyols are compounds with multiple active hydroxyl groups available for organic reactions and polymeric polyols are usually in a form of polyethers or polyesters. Most sugar alcohols are white, water-soluble natural occurring materials that are often used in the cosmetic, pharmaceutical and food industries as humectants, thickeners and sweeteners. They are represented by a general chemical formula $H(HCHO)_{n+1}H$, which is different from sugars' $H(HCHO)_nHCO$. Also, unlike sugars which tend to form ring structures, sugar alcohols do not. Yet, they can be dehydrated into cyclic ethers, e.g. sorbitol can be dehydrated to isosorbide. The sugar alcohols differ in chain length and have one hydroxyl (OH) group attached to each carbon (C) molecule in the chain. They are further differentiated by their relative orientation (stereochemistry) of these OH groups; for example, mannitol and sorbitol are isomers that share the same chemical formula $C_6H_8(OH)_6$ but are different in the orientation of the OH group on carbon 2 ($C^2$). The common types of sugar alcohols include, but not limited by, alditol, arabitol, erythritol, fucitol, galactitol, glycerol (or called glycerin), iditol, inositol, isomalt, lactitol, maltitol, mannitol, polyglycitol, sorbitol, threitol, volemitol and xylitol.

Figure 1:
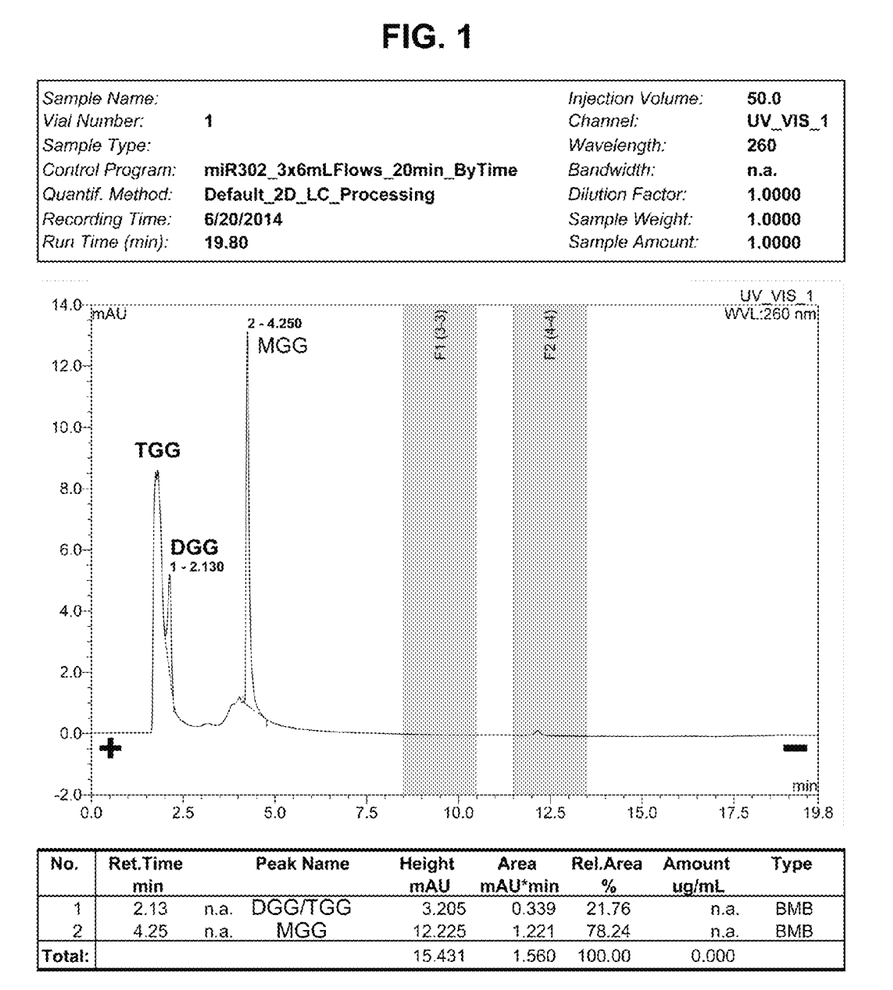
FIG. 1 shows the separation of DGG/TGG from MGG using HPLC purification.

Sugar alcohols can be separated into three major categories: monoglycylated glycerol (MGG), diglycylated glycerin (DGG), and triglycylated glyceride (TGG). Using high performance liquid chromatography (HPLC), we can isolate and collect pure MGG and partially mixed DGG and TGG (FIG. 1). Further stereochemical analysis has shown that the structure of MGG is similar to monosaccharides such as glucose, fructose and galactose, while those of DGG and TGG resemble disaccharides. In view of such similarity in structures, MGG may be used to replace monosaccharides for interfering with and reducing sugar absorption in diabetes patients.

The present invention identified and disclosed for the first time that novel sugar-like glycylated sugar alcohol compounds can be useful for treating Diabetes mellitus. Specifically, it is an object of the present invention to provide a method for treating the hyperglycemia symptoms and obesity problems of Diabetes mellitus, which comprises administering a composition comprising a glycylated sugar or glycylated sugar alcohol, wherein the glycylated sugar or glycylated sugar alcohol comes from at least one sugar alcohol or at least one sugar modified by the reaction of glycylation; wherein the at least one sugar alcohol has a formula of $H(HCHO)_{n+1}H$, and the at least one sugar has a formula of $H(HCHO)_nHCO$.

The present invention to provide a composition for developing treatments for hyperglycemia and obesity of Diabetes mellitus as well. The composition comprises a glycylated sugar or glycylated sugar alcohol, wherein the glycylated sugar or glycylated sugar alcohol comes from at least one sugar alcohol or at least one sugar modified by the reaction of glycylation; wherein the sugar alcohol has a formula of $H(HCHO)_{n+1}H$, and the sugar has a formula of $H(HCHO)_nHCO$.

DETAILED DESCRIPTION OF THE PREFERRED EMBODIMENT

Figure 2A:
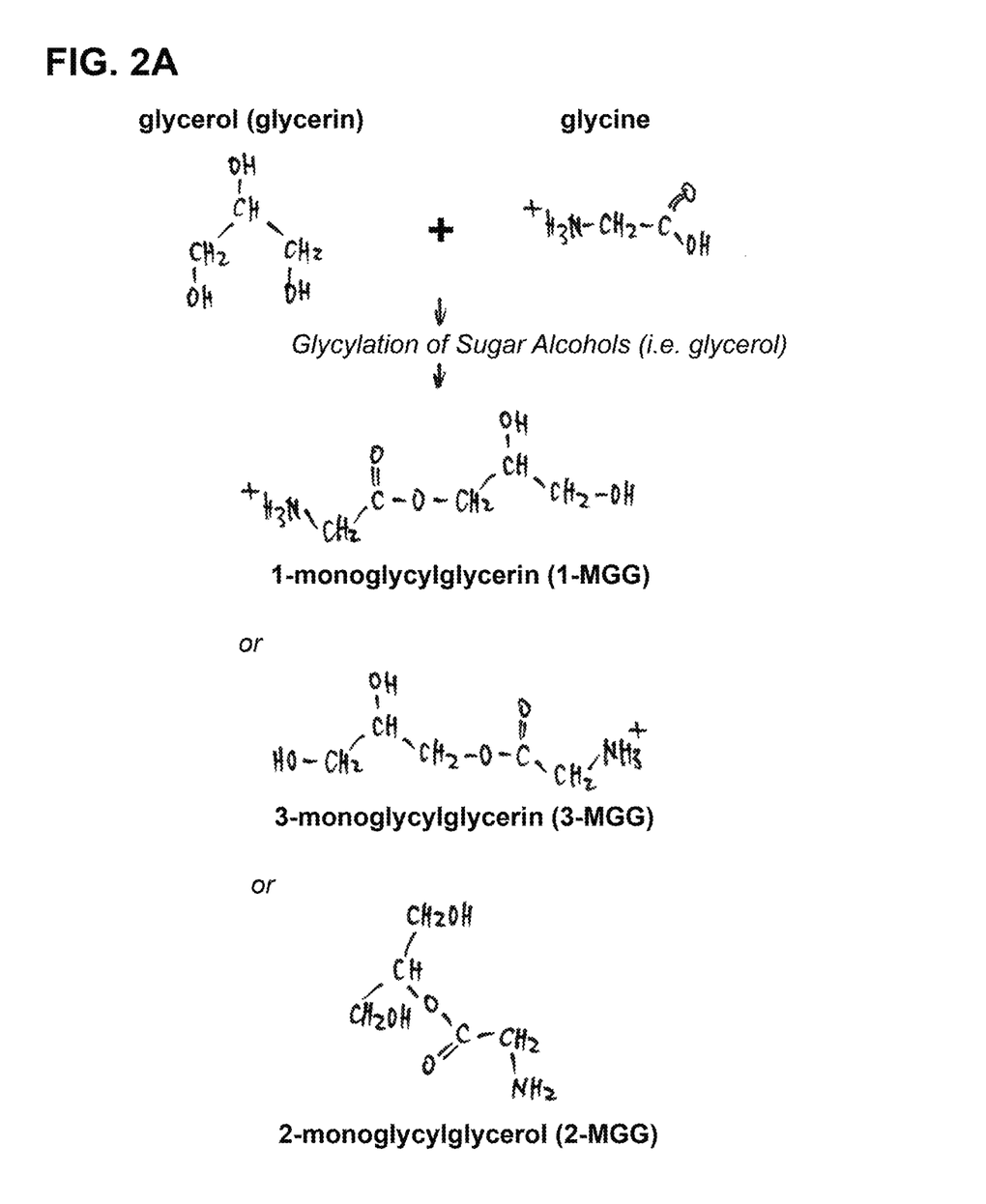
FIG. 2A shows the chemical reaction of glycylation at moderate dehydration and the resulting monoglycylated sugar alcohols (MGG) thereof, including 1-monoglycyl-glycerol, 3-monoglycylglycerol, and 2-monoglycylglycerin. The chemical formula for monoglycylglycerol is $NH_2CH_2CO(HCHO)_3H$ or $NH_3^+CH_2CO(HCHO)_3H$, depending on its pH condition.
Figure 2B:
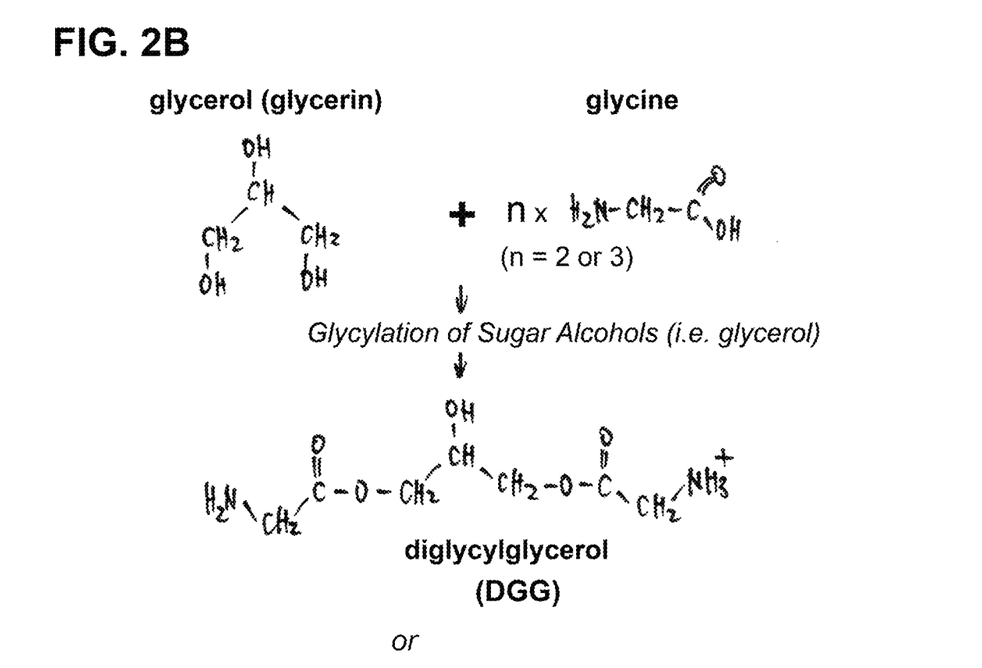
FIGS. 2B and 2C show glycylation after high levels of dehydration and the resulting diglycylated (DGG) and triglycylated sugar alcohols (TGG), respectively. For example, when glycerol (glycerin) is used as a model of sugar alcohol, two major kinds of highly glycylated products can be identified: one is diglycylglycerol (2B; DGG) and the other is 1,2,3-triglycylglyceride (2C; TGG).
Figure 2C:
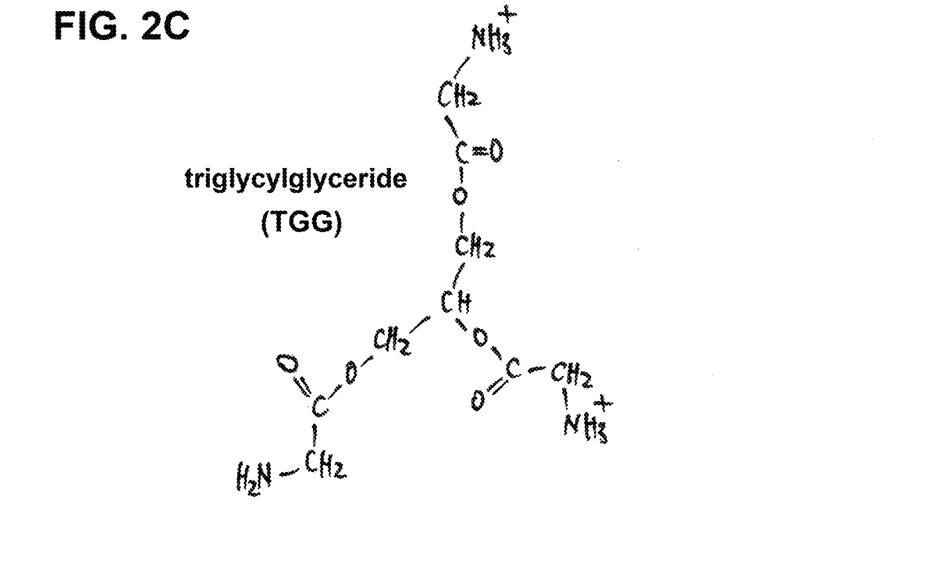

As shown in FIGS. 2A-2C, a novel chemical reaction—glycylation of sugar alcohols—has been developed to produce MGG, DGG and TGG. Previously, glycylation was only found to occur between amino acids but never in sugar alcohols or sugars. Yet, as defined here, glycylation is a chemical reaction that replaces the hydroxyl (HO—) groups of a sugar alcohol or sugar with glycine's glycyl ($NH_2CH_2COO$— or $NH_3^+CH_2COO$—) groups and thus results in the formation of an ether (R—O—R) linkage between each OH-removed carbon of the sugar/sugar alcohol and the glycyl group. This reaction involves a condensation process via dehydration. For example, when glycerol (or called glycerin) is used as a model of sugar alcohol, glycylation of glycerol will generate three kinds of reactive products: one is 1-, or 2-, or 3-monoglycylglycerol (MGG; FIG. 2A), another is 1,2-, or 2,3-, or 1,3-diglycylglycerol (DGG; FIG. 2B), and the last is 1,2,3-triglycylglyceride (TGG; FIG. 2C). In this model, glycylation can be a partial or completed reaction; for instance, MGG and DGG are partially glycylated products, while TGG is completely glycylated. Since MGG, DGG and TGG are all positively charged under acidic conditions, such as in the gastrointestinal (GI) system, and hence possess high affinity to glucose transporters (GLUT) that absorb sugars into cells. As a result, the binding of MGG/DGG/TGG to GLUT prevents sugar uptake via GLUT in the body, particularly in the GI system. By the same token, similar to sugar alcohols, simple sugars including glucose, fructose, galactose, sucrose and lactose may also be modified by glycylation and thus useful for reducing sugar uptake in diabetes patients as well.

Figure 3:
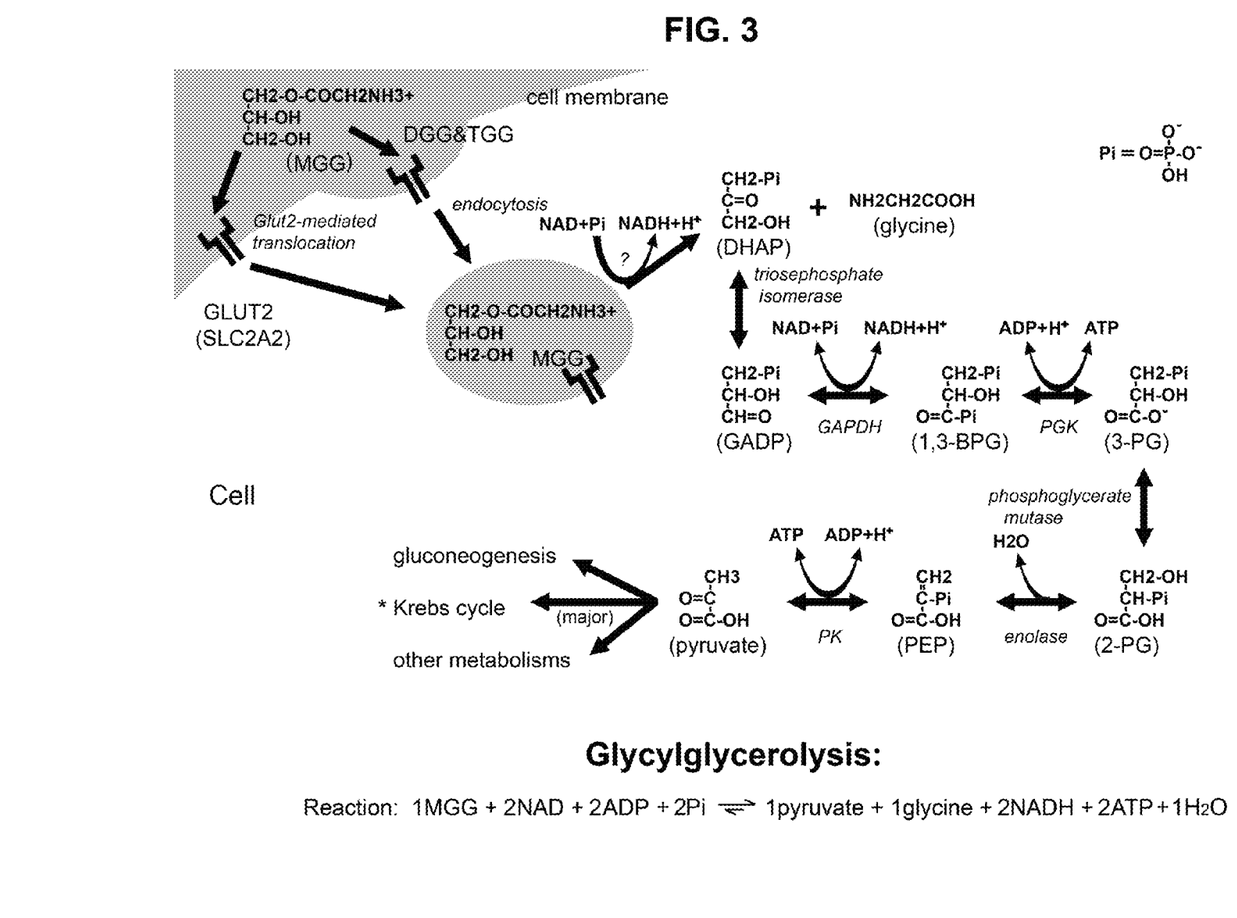
FIG. 3 shows the proposed metabolism of glycylated sugar alcohols such as MGG in cells. For example, due to structural similarity, MGG is absorbed via either GLUT2-mediated carrier transportation or endocytosis. After uptake by the cells, MGG is processed through a mechanism similar to glycolysis into pyruvate, which is then useful for other important biological metabolisms, such as Krebs cycle and gluconeogenesis.

Like natural sugars, these glycylated sugar alcohols can be absorbed by and into human cells via glucose transporters (GLUT) and/or GLUT-mediated endocytosis. For example, FIG. 3 shows that in human liver HepG2 cells the majority of MGG is absorbed by GLUT2 [also known as solute carrier family 2 (facilitated glucose transport), member 2 (SLC2A2)] through a protein conformational change and transporting mechanism. Yet, some MGG and the majority of DGG and TGG bind GLUT2 with high affinity and thus block the GLUT2 conformational change that is required for sugar influx. In this alternative pathway, the cells will then activate another endocytosis mechanism to internalize GLUT2 along with its bound MGG/DGG/TGG, leading to a decrease of GLUT2 on cell surface and hence reducing sugar uptake into GI tract cells.

The detail metabolism of glycylated sugar alcohols in cells, namely "glycylglycerolysis", is proposed in FIG. 3. After absorbed by the cells, glycylated sugar alcohols such as MGG will be first processed into dihydroxyacetone phosphate (DHAP) and then turned into its isomer D-glyceraldehyde-3-phosphate (GADP). After that, glyceraldehyde phospahte dehydrogenase (GAPDH) converts GADP into D-1,3-bisphosphoglycerade (1,3-BPG), which is subsequently converted by phosphoglycerate kinase (PGK) into 3-phosphoglycerate (3-PG), by phosphoglycerate mutase (PGM) into 2-phosphoglycerate (2-PG), and then further by enolase into phosphoenolpyruvate (PEP). Last, after PEP is converted into pyruvate by a kinase (PK), this end product—pyruvate—can be finally utilized by the cells for generating energy (via Kreb's cycle or citric acid cycle), producing sugars (via gluconeogenesis), and being involved in other cellular metabolisms. As a result, these glycylated sugar alcohols not only can lower blood sugar levels in diabetes patients but also can serve as an alternative energy source for preventing acute hypoglycemia that has often seen in overdose of other anti-diabetic drugs, such as alpha-glucosidase inhibitors.

Since glycylated sugar alcohols function through reduction of sugar absorption in human GI systems, oral administration is the best way to deliver this kind of medicine.

Also, because the raw materials to make glycylated sugar alcohols are sugar alcohols and glycine, both of which are food supplements, this drug has been tested and shown no sign of toxicity or hypoglycemia up to 1 g in mouse (1/40 of the body weight). Yet, at high dosage (>0.65 g per mouse), mild to moderate diarrhea may be observed in 15%-20% of the tested mice post-meal. To further test its drug effects in treating diabetes and obesity, we had fed 1 mg (in 1 mL) of purified MGG to each of C57BL/6J diet-induced diabetic mice (n=3) right before meal, while C57BL/6J mice fed with 1 mL of ddH$_2$O were served as controls (n=3). After drug administration, each mouse was fed with a high carbohydrate mixture of 4 mg glucose and 2 g Kaytee mouse food for a single meal. Then, whole blood sugar levels were measured at 0, 0.5, 1, 1.5, 2, 2.5, 3, 3.5, and 4 hours (hr) post-meal, using a Bayer Contour Next USB system. No water uptake during this 4-hour measurement period of time.

Figure 4:
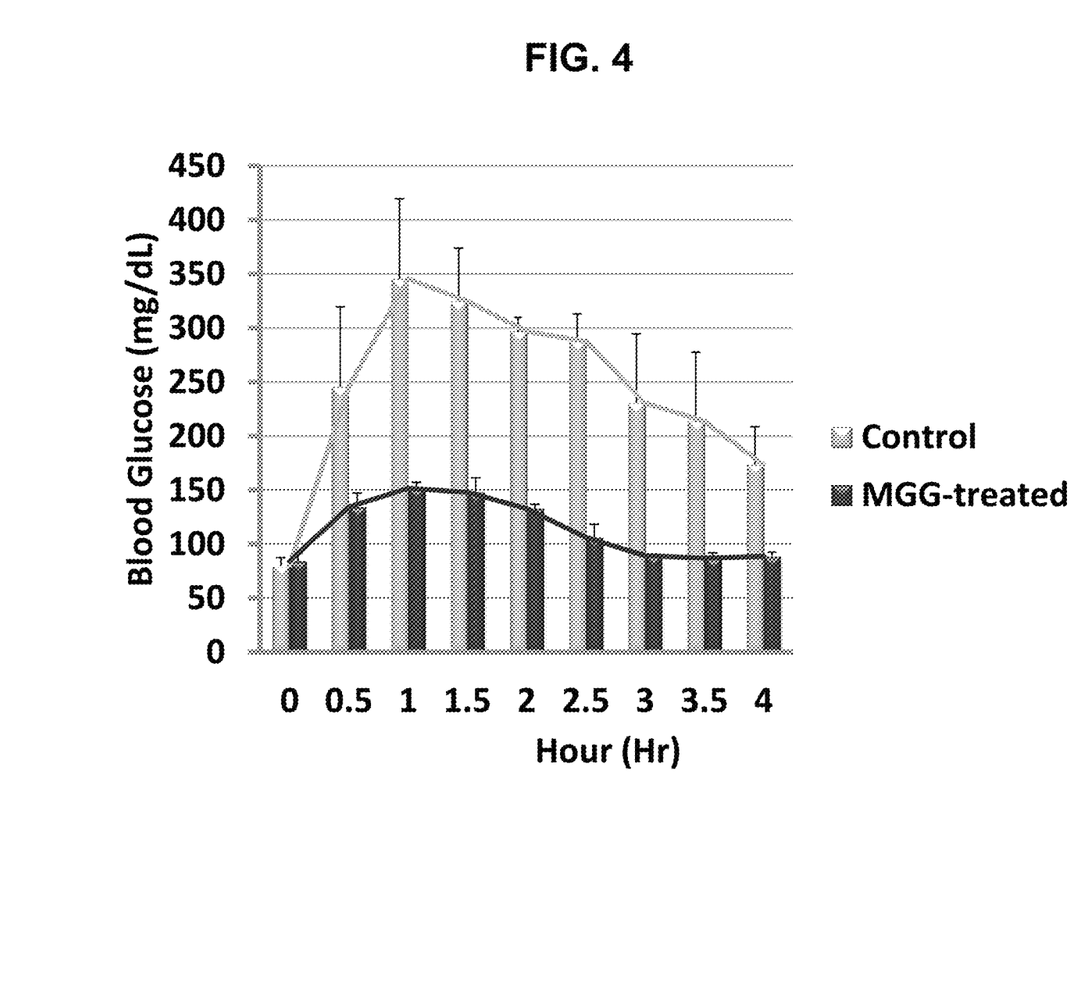
FIG. 4 shows the therapeutic effects of glycylated sugar alcohol-containing anti-diabetic drugs on the hyperglycemia symptoms of diabetic mice in vivo. (male, 8-week-old C57BL/6J, total n=6).

The results of blood sugar level changes were shown in FIG. 4. For MGG-treated mice, the blood glucose levels were measured as 85, 91, 77 mg/dL (average 84.3±7.0 mg/dL) at 0 hr, 135, 147, 121 mg/dL (average 134.3±13.0 mg/dL) at 0.5 hr, 157, 151, 147 mg/dL (average 151.7±5.5 mg/dL) at 1 hr, 155, 131, 158 mg/dL (average 148±13.4 mg/dL) at 1.5 hr, 129, 137, 133 mg/dL (average 133±4.0 mg/dL) at 2 hr, 97, 121, 101 mg/dL (average 106.3±12.0 mg/dL) at 2.5 hr, 91, 89, 88 mg/dL (average 89.3±1.5 mg/dL) at 3 hr, 93, 85, 83 mg/dL (average 87±5.0 mg/dL) at 3.5 hr, and 88, 93, 85 mg/dL (average 88.7±4.0 mg/dL) at 4 hr, respectively. As all detected numbers are comparably similar to those from normal persons after meal, we concluded that the treatment of glycylated sugar alcohols such as MGG obviously can maintain normal-like blood sugar levels after high carbohydrate meal in diabetes individuals. On the other hand, for untreated control mice, the blood glucose levels were measured as 73, 79, 88 mg/dL (average 80±7.5 mg/dL) at 0 hr, 255, 167, 315 mg/dL (average 245.7±74.0 mg/dL) at 0.5 hr, 375, 267, 415 mg/dL (average 345.7±74.0 mg/dL) at 1 hr, 315, 281, 379 mg/dL (average 325±49.0 mg/dL) at 1.5 hr, 295, 285, 311 mg/dL (average 297±13.0 mg/dL) at 2 hr, 264, 284, 315 mg/dL (average 287.7±25.5 mg/dL) at 2.5 hr, 171, 222, 299 mg/dL (average 230.7±64.0 mg/dL) at 3 hr, 157, 199, 285 mg/dL (average 213.7±64.0 mg/dL) at 3.5 hr, and 143, 166, 213 mg/dL (average 173.7±35.0 mg/dL) at 4 hr, respectively. After we further compared the detected numbers between MGG-treated and untreated mice, the results clearly showed that the treatment of glycylated sugar alcohols significantly lowers the absorption of glucose into blood stream and hence successfully prevents the hyperglycemia symptoms in diabetes animals in vivo.

Figure 5:
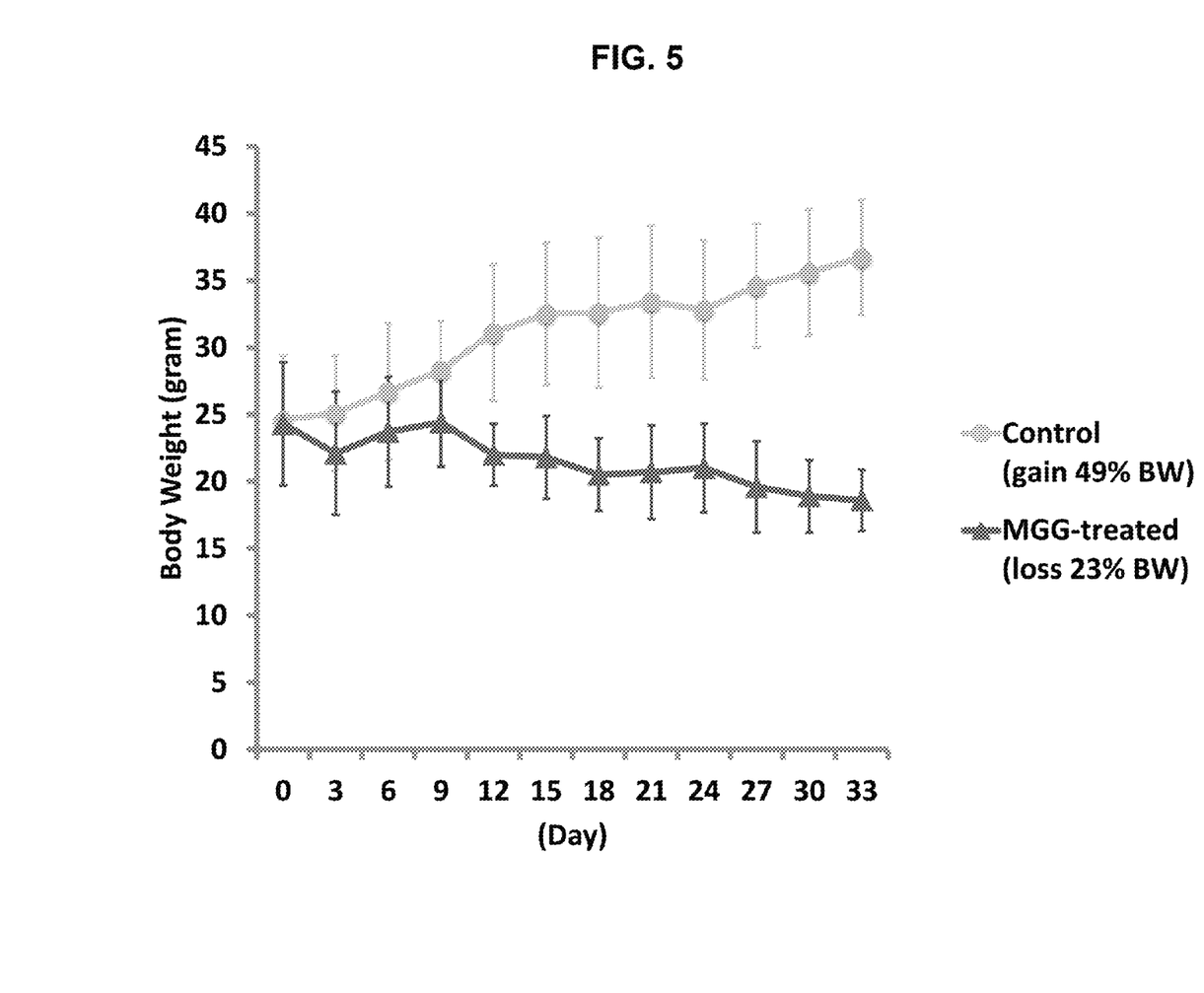
FIG. 5 shows the effects of glycylated sugar alcohol treatments on the changes of body weight of diet-induced obesity mice in vivo (male, 8-week-old C57BL/6J, total n=6).

In addition, loss of body weight has also been observed in MGG-treated mice but not controls. As shown in FIG. 5, diabetic C57BL/6J mice (n=3) treated with 1 mg of MGG (in 1 mL ddH$_2$O) before every meal (3 high carbohydrate meals per day) for about one month have been found to lose about 16% to 30% (average 23%) of body weights, whereas those controls (n=3) treated with only 1 mL ddH$_2$O gained average over 49% of body weights. Clearly, this result further indicates another potential use of glycylated sugar alcohols in treating obesity, in particular diabetes-related obesity in vivo.

In view of all above evidences, we have practically enabled the use of a novel glycylated sugar alcohol composition for not only treating the hyperglycemia symptoms and obesity problems in diabetes individuals but also preventing the risk of hypoglycemia that is often seen in other anti-diabetic drugs. As a result, this kind of new medicine by competing against monosaccharides to block or reduce sugar uptake in the GI system may lead to a safer and more effective treatment for diabetes patients. In particular, since it is noted that all materials used to produce these glycylated sugar alcohol compositions are totally non-toxic and safe under Food and Drug Administration (FDA) regulations, this new kind of anti-diabetic drugs may also be used as a food supplement for maintaining the daily care of diabetes patients.

A. Definitions

To facilitate understanding of the invention, a number of terms are defined below:

Treated Cell: a single or a plurality of human or animal cells selected from the group consisting of a somatic cell, a tissue cell, a stem cell, a germ-line cell, a tumor cell, a cancer cell, and a combination thereof.

Glycylation: a chemical reaction that replaces the hydroxyl (HO—) groups of a sugar alcohol or sugar with glycine's or glycylated amino acid's glycyl (NH$_2$CH$_2$COO— or NH$_3^+$CH$_2$COO—) groups and thus results in the formation of an ether (R—O—R) linkage between each OH-removed carbon of the sugar alcohol/sugar and the glycyl group of the glycine and/or glycylated amino acid.

Pharmaceutical and Therapeutic Application: a biomedical utilization, treatment method, device and/or apparatus useful for diagnosis, stem cell generation, stem cell research and/or therapy development, tissue/organ repair and/or rejuvenation, wound healing treatment, tumor suppression, cancer therapy and/or prevention, disease treatment, diabetes and obesity treatment, drug production, and a combination thereof.

Prokaryotes: a one-cell organism that lacks a distinct membrane-bound nucleus and has its genetic materials in the form of a continuous strand of DNA, such as bacteria and archaea.

Eukaryote or Eukaryotic Cell: an one-cell or multiple-cell organism whose cells contain a nucleus and other structures (organelles) enclosed within membranes, such as yeast, plant and animal cells.

B. Compositions and Applications

The present invention discloses a novel glycylated sugar alcohol composition and its use for treating the hyperglycemia symptoms and obesity problems of Diabetes mellitus, comprising at least a sugar alcohol or sugar modified by the reaction of glycylation.

In addition, the present invention also teaches a novel method of glycylation and its use for producing positively charged sugar alcohol and sugar compounds capable of interacting with negatively charged materials such as cell surface receptors and transmembrane transporters via electrostatic affinity and/or structural similarity.

In the present invention, the disclosure of glycylated sugar alcohol/sugar compositions and the reaction of glycylation in sugar alcohols and sugars have been first reported in our claimed priority of U.S. Ser. No. 14/457,829 filed on Aug. 12, 2014, entitled "Novel Sugar Alcohol-Based Compositions for Delivering Nucleic Acid-Based Drugs In Vivo and In Vitro". Furthermore, the use of these glycylated sugar alcohols and/or sugars for treating diabetes and obesity is totally novel and never been reported before. As the metabolism of these glycylated sugar alcohols is revealed in the present invention for the first time, the knowledge disclosed will be very useful for developing medicines and/or food supplements for treating related metabolic diseases, such as diabetes and obesity.

BRIEF DESCRIPTION OF THE DRAWINGS

Referring particularly to the drawings and examples for the purpose of illustration only and not limitation, there is illustrated.

EXAMPLES

In the experimental disclosure which follows, the following abbreviations apply: M (molar); mM (millimolar); µm (micromolar); mol (moles); pmol (picomoles); gm (grams); mg (milligrams); µg (micrograms); ng (nanograms); L (liters); mL (milliliters); µL (microliters); ° C. (degrees Centigrade); RNA (ribonucleic acid); DNA (deoxyribonucleic acid); dNTP (deoxyribonucleotide triphosphate); PBS (phosphate buffered saline); NaCl (sodium chloride); HEPES (N-2-hydroxyethylpiperazine-N-2-ethanesulfonic acid); HBS (HEPES buffered saline); SDS (sodium dodecyl sulfate); Tris-HCl (tris-hydroxymethylaminomethane-hydrochloride); ATCC (American Type Culture Collection, Rockville, Md.); hESC (human embryonic stem cells); and iPSC (induced pluripotent stem cells).

1. Production of Glycylated Sugar Alcohol Compositions

Although the natural mechanism of sugar/sugar alcohol glycylation is unclear, we have developed a chemical protocol and method to artificially make glycylated sugar alcohols and glycylated sugars. First, a solution was prepared, containing 1.0 M glycerol or fructose and 0.9% (w/v) NaCl in dd$H_2O$. Then, glycine was added into the solution to reach a final concentration of 0.05~3.0 M, depending on the desired concentration of final glycylated sugar alcohols/sugars, and mixed well. After overnight incubation at 4° C. with constant agitation, the glycine-added solution was heated at a temperature over 45° C., preferably >94° C., till the water ($H_2O$) content to be almost completely vaporized. This dry-style dehydration protocol usually generated about 35% of MGG and about 65% of DGG/TGG. Before use, the final concentration of these glycylated sugar alcohols could be adjusted simply by adding a desired amount of autoclaved dd$H_2O$ to dissolve the dry reaction products. Alternatively, in order to increase the MGG production rate, we further designed a wet-style dehydration protocol, using autoclave machine. Different from the aforementioned, after mixing glycine with the glycerol and NaCl solution, the mixture was then placed into an autoclave machine and run in a dry sterilization cycle at about 121° C. and 100 kPa. After autoclave cycle was completed, the reaction would contain about 78% of MGG and about 22% of DGG/TGG. Before use, the final concentration of the glycylated sugar alcohols could be adjusted by adding a desired amount of autoclaved dd$H_2O$ into the reaction. The chemical structures of MGG, DGG and TGG are shown in FIGS. 2A-2C.

2. Human Cell Culture and Treatment

Human liver cell line HepG2 was obtained from ATCC and cultivated at 37° C. under 5% $CO_2$, according to manufacturer's suggestions.

3. High Performance Liquid Chromatography (HPLC) Analysis

A reverse-phase HPLC method has been developed for separating MGG from DGG and TGG, based on their different charges. HPLC programs were run by an Ultimate 3000 HPLC machine (Thermo Scientific) with a DNA Pac PA-100 column (BioLC Semi-Prep 9×250 mm) at a flow rate of 3.6 mL/min. Starting buffer was 50 mM Tris-HCl (pH7.6) and mobile buffer was 50 mM Tris-HCl (pH7.6) with 500 mM sodium perchlorate. Signals of differently charged glycylated sugar alcohols were detected with an UV detector at 260 nm. The results were shown in FIG. 1.

4. In Vivo Evaluation of Glycylated Sugar Alcohol-Treated Diabetic Mice

To test the drug effects of MGG in treating diabetes, we had fed 1 mg (in 1 mL) of purified MGG to each of C57BL/6J diet-induced diabetic mice (male, 8-week-old, n=3) right before meal. C57BL/6J mice fed with 1 mL of dd$H_2O$ were served as control (male, 8-week-old, n=3). After drug administration, each mouse was fed with a high carbohydrate mixture of 4 mg glucose and 2 g Kaytee mouse food for a single meal. Then, whole blood sugar levels were measured at 0, 0.5, 1, 1.5, 2, 2.5, 3, 3.5, and 4 hours (hr) post-meal, using a Bayer Contour Next USB detector system. Neither food nor water was given to those mice 4-hour before treatment and 4-hour post-meal. Yet, during each meal, another additional 2 mL of dd$H_2O$ was given to each mouse. The results were shown in FIG. 4.

5. In Vivo Evaluation of Glycylated Sugar Alcohol-Treated Obesity Mice

To test the drug effects of MGG in treating obesity, we had fed 1 mg (in 1 mL) of purified MGG to each of C57BL/6J diet-induced obesity mice (male, 8-week-old, n=3) right before meal, while C57BL/6J mice fed with 1 mL of dd$H_2O$ were served as controls (male, 8-week-old, n=3). After drug administration, each mouse was fed with a high carbohydrate mixture of 4 mg glucose and 2 g Kaytee mouse food for a single meal. Each mouse was treated and fed three times per day for about one month. Water (dd$H_2O$) was provided all time without limits. The results were shown in FIG. 5.

6. Statistic Analysis

Any change over 10% of signal intensity was considered as a positive result, which in turn was analyzed and presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ was considered significant. All p values were determined from two-tailed tests.

REFERENCES

1. Chen S K J and Lin S L. (2013) Recent patents on microRNA-induced pluripotent stem cell generation. *Recent Patents on Regenerative Medicine* 3, 5-16.
2. Lin S L, Chang D, Chang-Lin S, Lin C H, Wu D T S, Chen D T, and Ying S Y. (2008) Mir-302 reprograms human skin cancer cells into a pluripotent ES-cell-like state. *RNA* 14, 2115-2124.
3. Lin et al. (2011). Regulation of somatic cell reprogramming through inducible mir-302 expression. *Nucleic Acids Res.* 39, 1054-1065.
4. Lin S L, Chang D, Ying S Y, Leu D, and Wu D T S. (2010) MicroRNA miR-302 inhibits the tumorigenecity of human pluripotent stem cells by coordinate suppression of CDK2 and CDK4/6 cell cycle pathways. *Cancer Res.* 70, 9473-9482.
5. Suez et al., (2014) Artificial sweeteners induce glucose intolerance by altering the gut microbiota. *Nature* in press, doi:10.1038/nature13793.

The invention claimed is:

1. A method for treating the hyperglycemia symptoms and obesity problems of diabetes mellitus, comprising administering a composition comprising a glycylated sugar alcohol or a glycylated sugar to a subject suffering from hyperglycemia symptoms or obesity problems of diabetes mellitus, wherein the glycylated sugar alcohol or the glycylated sugar comes from at least one sugar alcohol or at least one sugar modified by the reaction of glycylation; wherein the at least one sugar alcohol has a formula of $H(HCHO)_{n+1}H$, and the at least one sugar has a formula of $H(HCHO)_nHCO$, wherein the composition comprising said glycylated sugar alcohol or said glycylated sugar contains monoglycylglycerol (MGG).

2. The method as defined in claim 1, wherein said glycylation is a chemical reaction in that at least one hydroxyl (—OH) group of the sugar alcohol or the sugar is replaced by at least one glycyl ($NH_3^+CH_2COO$—) group from a glycine or a glycylated amino acid and results in formation of an ether (R—O—R) linkage between each OH-removed carbon of the sugar alcohol or the sugar and each of the glycyl groups.

3. The method as defined in claim 1, wherein said sugar alcohol is glycerol or said sugar is fructose.

4. The method as defined in claim 1, wherein said monoglycylglycerol has a chemical formula of $NH_3^+CH_2CO(HCHO)_3H$.

5. The method as defined in claim 1, wherein said glycylated sugar alcohol or said glycylated sugar is positively charged.

6. The method as defined in claim 1, wherein said glycylated sugar alcohol or said glycylated sugar is administered orally.

7. The method as defined in claim 1, wherein said glycylated sugar alcohol or said glycylated sugar is further in solution and has a concentration ranged from 0.1 μM to 10 M.

8. The method as defined in claim 1, wherein said glycylated sugar alcohol or said glycylated sugar competes with monosaccharides for intestinal absorption in vivo.

9. The method as defined in claim 1, wherein said glycylated sugar alcohol or said glycylated sugar interferes with sugar absorption in intestines.

10. The method as defined in claim 1, wherein said glycylated sugar alcohol or said glycylated sugar is absorbed into cells via glucose transporters.

11. The method as defined in claim 1, wherein said glycylated sugar alcohol or said glycylated sugar is a food supplement.

12. The method as defined in claim 1, wherein said glycylated sugar alcohol or said glycylated sugar reduces glucose absorption in vivo and prevents the hyperglycemia symptoms and the obesity problems of diabetes mellitus.

13. The method as defined in claim 1, wherein said glycylated sugar alcohol or said glycylated sugar is a part of an active ingredient in the preparation of anti-diabetic drugs.

14. The method as defined in claim 1, wherein said glycylated sugar alcohol or said glycylated sugar is a part of an active ingredient in the preparation of anti-obesity drugs.

15. The method as defined in claim 1, wherein said glycylated sugar alcohol or said glycylated sugar is a part of an active ingredient in the preparation of substances for cosmetic, pharmaceutical and therapeutic applications.

* * * * *